United States Patent
Kurz et al.

(10) Patent No.: US 6,387,128 B1
(45) Date of Patent: May 14, 2002

(54) AUDITORY OSSICLES PROSTHESIS

(75) Inventors: Heinz Kurz, Dusslingen; Walter Gamer, Bruchsal, both of (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 09/432,953

(22) Filed: Nov. 3, 1999

(30) Foreign Application Priority Data

Nov. 6, 1998 (DE) ..................... 298 19 892 U

(51) Int. Cl.$^7$ .................................................. A61F 2/18
(52) U.S. Cl. ........................................................ 623/10
(58) Field of Search ............................. 623/10; 606/207

(56) References Cited

U.S. PATENT DOCUMENTS

| | | | | |
|---|---|---|---|---|
| 4,641,651 A | * | 2/1987 | Card ............................. | 623/10 |
| 4,655,776 A | * | 4/1987 | Lesinski ....................... | 623/10 |
| 4,921,498 A | * | 5/1990 | Bays et al. ................... | 623/10 |
| 5,059,214 A | * | 10/1991 | Akopov et al. .............. | 606/207 |
| 5,104,401 A | * | 4/1992 | Kurz ............................. | 623/10 |
| 5,180,391 A | | 1/1993 | Beoni | |
| 5,554,188 A | | 9/1996 | Prescott | |
| 5,814,104 A | | 9/1998 | Beoni | |
| 6,001,120 A | * | 12/1999 | Levin .......................... | 606/207 |
| 6,168,625 B1 | * | 1/2001 | Prescott ....................... | 623/10 |

FOREIGN PATENT DOCUMENTS

| | | |
|---|---|---|
| DE | 197 44 789 A1 | 4/1998 |
| DE | 298 02 776 U1 | 5/1998 |
| EP | 0 563 767 A1 | 10/1993 |
| FR | 2 721 199 | 12/1995 |
| WO | 92/18066 | 10/1992 |

* cited by examiner

Primary Examiner—Bruce Snow
Assistant Examiner—Brian E. Pellegrino
(74) Attorney, Agent, or Firm—Michael J. Striker

(57) ABSTRACT

An auditory ossicles prosthesis has a head plate for abutment against an eardrum, and a shaft arranged on said head plate for bridging a tympanic cavity from the eardrum up to a stirrup or a stirrup footplate, and the head plate has a throughgoing passage through which the shaft can be pushed more or less so as to be cut at an opposite side of the head plate to a desired length, and then the passage is narrowed to fix the shaft in its final position.

11 Claims, 2 Drawing Sheets

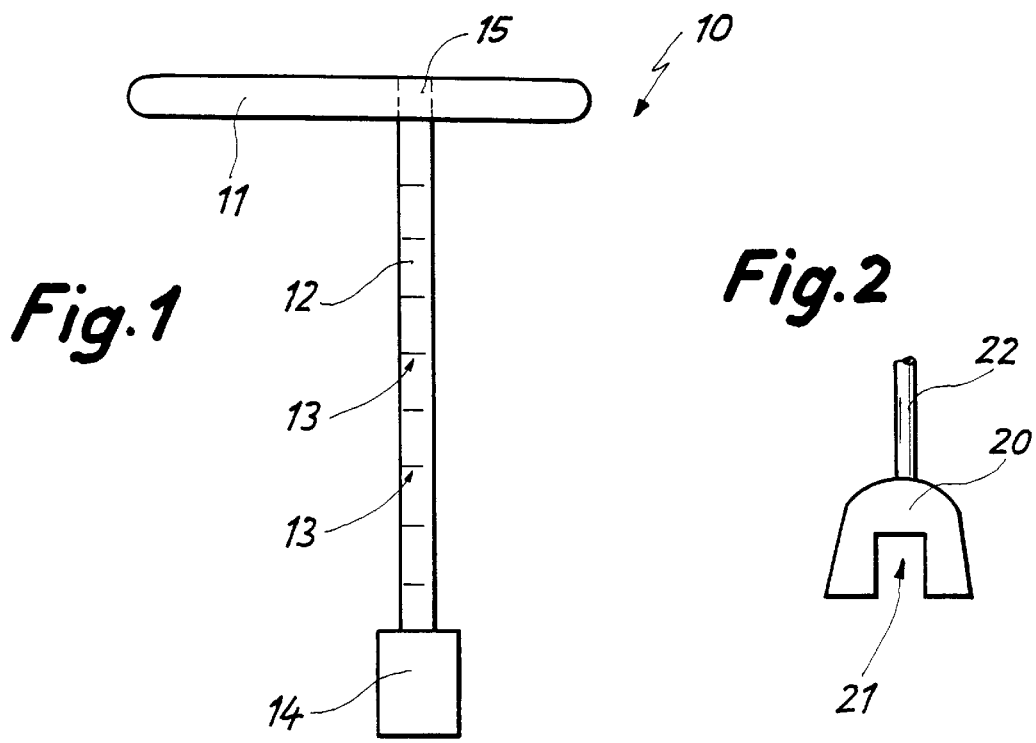
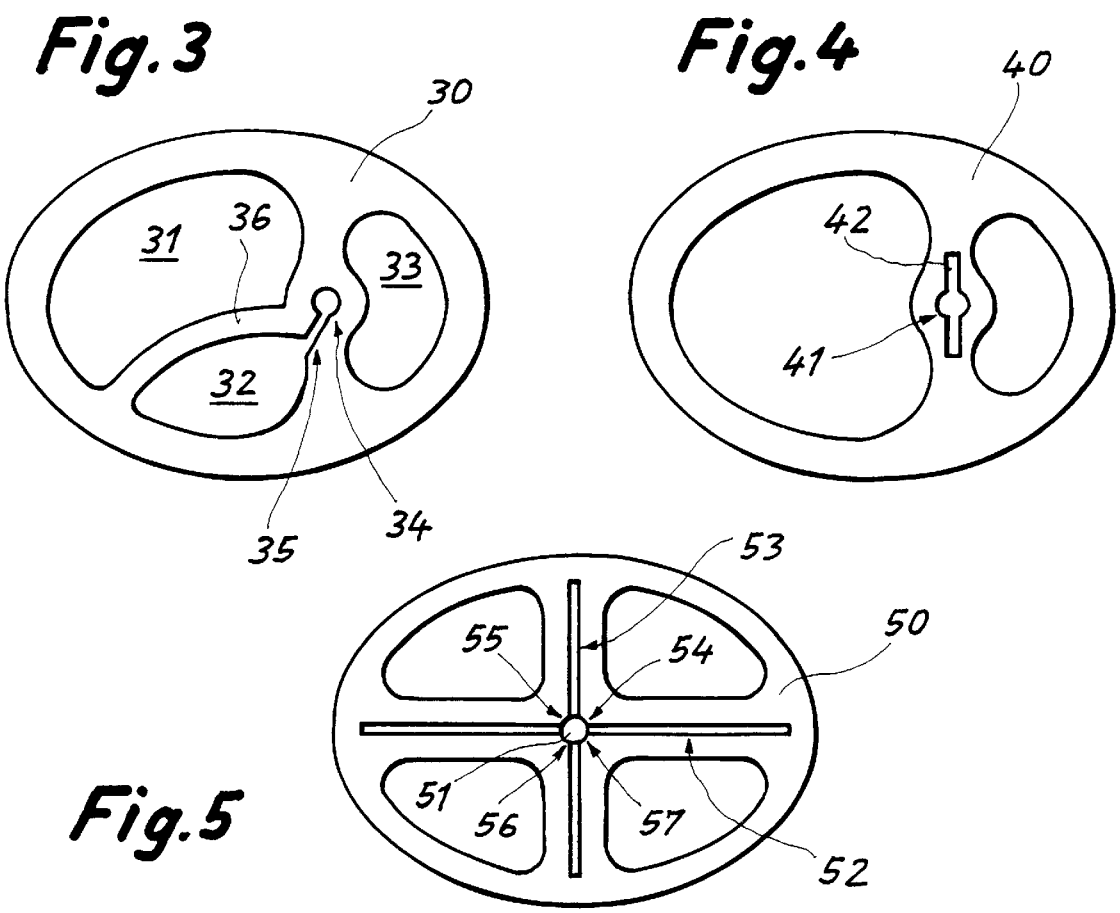

AUDITORY OSSICLES PROSTHESIS

BACKGROUND OF THE INVENTION

The present invention relates generally to auditory ossicles prostheses. More particularly, it relates to an auditory ossicles prostheses with a head plate for abutting against an eardrum and a shaft arranged on it for bridging the timpanic cavity from the eardrum up to a stirrup or up to stirrup foot plate, wherein the shaft is provided with a coupling member at its end facing the stirrup.

For the implantation of the auditory ossicles prosthesis, before the implantation it is necessary to determine the length of the prosthesis individually for corresponding patients. Since the required length can be determined first only during the operation, for each operation either a set of prostheses of different lengths or a prosthesis with a variable shaft length are needed. In known, longitudinally adjustable auditory ossicles prostheses, the shaft of the prosthesis is subdivided into a plurality of successive portions, and the successively arranged portions are separated from one another by a cross-sectional reduction at predetermined breaking points. Since with fine auditory ossicles prostheses it is necessary to operate in the region of tenths or hundredths millimeters, the manufacture of the predetermined breakage points is relatively complicated and expensive.

SUMMARY OF THE INVENTION

Accordingly, it is an object of present invention to provide an auditory ossicles prosthesis of the above mentioned general type, which is improved so that the separation of the shaft into the individual lengths can be performed with lower manufacturing expenses for the shaft and thereby cost reduction can be obtained.

In keeping with these objects and with others which will become apparent hereinafter, one feature of present invention resides, briefly stated, in an auditory ossicles prostheses in which the head plate has a throughgoing opening for receiving the shaft, and the opening is narrowerable for fixing the shaft. For shortening of the shaft, it is displaced through the opening in the head plate, so that it extends outwardly beyond the outer side of the head plate, so that it can project at the outer side of the head plate and can be cut off there. Subsequently, the opening of the head plate is reduced and thereby the shaft is fixed reliably. Then the adjusted prosthesis can be implanted.

When the auditory ossicles prosthesis is designed in accordance with the present invention, it can be adjusted in a fast and stepless manner to the anatomical characteristics of the patient. For narrowing the opening in the head plate, there are several possibilities.

The periphery of the opening can be interrupted by a slot, and the slot and thereby the opening can be narrowed via a deformable web caulking. Thereby the shaft can be fixed on the head plate fast and with less expense. For the same reason the opening can be provided in the center with a slot, and the opening can be narrowed by compressing the slot. The opening can be located also in the center of two intersecting slots, in which case the opening has a smaller diameter than the shaft diameter.

In order to provide an optimal abutment of the head plate on the ear drum, it can be elliptic or can have rounded edges.

Also, it can have at least one passage for controlling the position of the coupling piece by an operator.

In accordance with a further embodiment, the shaft can be provided with a scale. This will facilitate the adjustment of the length of the shaft.

The auditory ossicles prosthesis can be roughened at the side which faces the eardrum and/or stirrup. This provides for an optimal abutment of the auditory ossicles prosthesis against the eardrum or the stirrup.

The components and the whole auditory ossicles prosthesis can be produced by a laser technology. This approach will reduce the manufacturing costs.

The auditory ossicles prosthesis of the invention can be composed of gold and/or titanium. As a result it becomes compatibile with users bodies.

The coupling member of the auditory ossicles prosthesis of the invention can be formed as a bell-shaped structure or as a plunger. Thereby the auditory ossicles prosthesis can be mounted reliably both as a total prosthesis or also as a partial prosthesis on the stirrup. When the bell-shaped coupling member is used, it can be slotted for guaranteeing an optimal hold on the stirrup. The slot can extend parallel to the longitudinal semi-axis of the elliptic head plate. In the bell-shaped structure the slot can have a width preferably of 0.6 mm.

When the prosthesis is formed as a total prosthesis with a plunger-shaped coupling member, it can have a diameter of 0.8 mm and can be provided with a hollow space, to obtain reliable seat on the stirrup foot plate.

For adjusting the shaft length of the auditory ossicles prosthesis of the present invention, a tool is proposed which has two articulately connected legs, with the thickness of the legs changing in a stepped manner over the leg length. At the inner side of the legs depressions are provided for receiving the shaft, and also lateral depressions are provided for receiving the head plate. The shaft of the auditory ossicles prosthesis can be inserted into one of the depressions for receiving the shaft, and in particular at one of the stages of the leg of the tool whose thickness exactly corresponds to the desired length of the shaft. In this way the tool for adjusting the shaft length also has the function of a gauge.

With the special tool and the individually length-adjustable shaft, the shaft length of the auditory ossicles prosthesis during the operation can be adjusted in a shortest time to the exact measurements in the ear of the patient.

The depressions can be formed on the contact-surface to the other leg as semi-circular recesses. Therefore the shaft can be introduced optimally in the depressions at the contact surface to the other leg.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a side view of an auditory ossicles prosthesis in accordance with the present invention;

FIG. 2 is a detail view of a coupling member of the inventive auditory ossicles prosthesis;

FIG. 3 is a plan view of the head plate of the inventive auditory ossicles prosthesis;

FIG. 4 is a plan view of a second embodiment of the head plate of the inventive auditory ossicles prosthesis;

FIG. 5 is a plan view in accordance with a third embodiment of a head plate of the inventive ossicles prosthesis;

DESCRIPTION OF PREFERRED EMBODIMENTS

Figure 6:
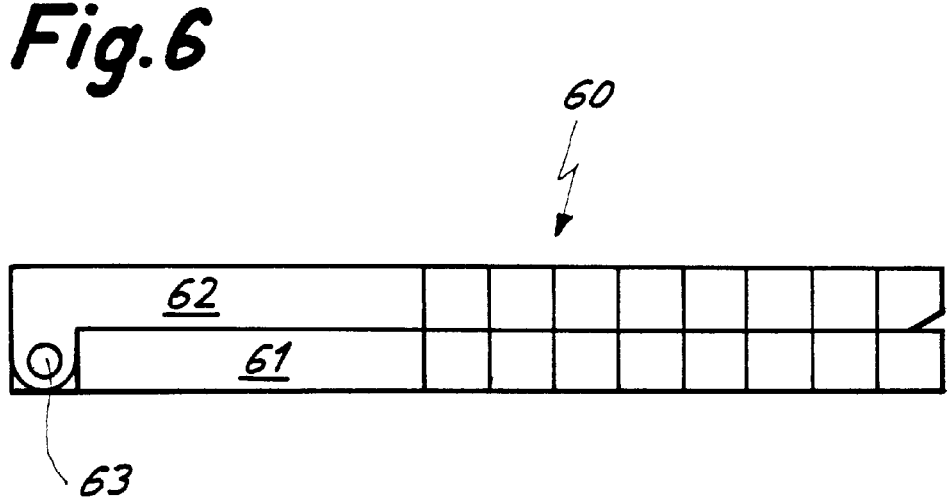
FIG. 6 is a plan view of a tool for adjusting the shaft length of the auditory ossicles prosthesis of the invention.

FIG. 1 shows an auditory ossicles prosthesis which is identified as a whole with reference numeral 10. It has a head plate 11 which abuts against an eardrum. A shaft 12 is arranged on the head plate 11 in an opening 15 it bridges the tympanic hole of the eardrum up to the stirrup or up to the stirrup footplate. The shaft 12 has a scale 13 for determining a desired shaft length. A plunger 14 is provided on the lower end of the shaft 12 for the use as a total prosthesis. The plunger 14 is arranged during the implantation on the stirrup foot plate.

FIG. 2 shows a detailed view of a bell-shaped coupling member 20. The coupling member 20 is utilized for the use of the prosthesis as a partial prosthesis and is arranged on the stirrup. For providing an optimal seat of the coupling member 20 on the stirrup, the coupling member 20 has a slot 21. The coupling member 20 is mounted on a shaft 22.

FIG. 3 shows a head plate which abuts against the eardrum. The head plate 30 has an oval shape and is roughened on the side which faces the eardrum so as to provide an optimal abutment against the eardrum. It has openings 31, 32, 33. The shaft 12, 22 of the inventive auditory ossicles prosthesis 10 can pass through a passage 34. The periphery of the passage 34 is interrupted by a slot 35. The slot 35 and thereby the opening 34 can be reduced by a deformable web 36 by caulking of the web 36. In this way the shaft which is inserted in the passage 34 is fixed. When the opening 34 is not reduced, the shaft 12, 22 can displace through the opening 34 so that its end extends at the outer side of the head plate 30 and can be cutoff.

FIG. 4 shows another embodiment of a head plate 40. It has an opening 41 in the center of a slot 42. The shaft which is inserted in the opening 41 can be fixed by compressing the slot 42 and the opening 41.

FIG. 5 shows another embodiment of a head plate 50 which has an opening 51 in the center of two intersecting slots 52 and 53. A shaft of an auditory ossicles prosthesis passes through the opening 51 and its diameter is greater than the diameter of the opening 51. The shaft can be wedged against the passing direction at the rounded edges 54, 55, 56 and 57. Thereby it is fixed opposite to the passing direction. As can be seen from FIGS. 3–5, the slots and the webs can have different shapes.

FIG. 6 shows a tool 60 for adjusting the shaft length of an auditory ossicles prosthesis. The tool 16 includes two legs 61 and 62 which are connected with one another by a hinge 63.

Figure 7:
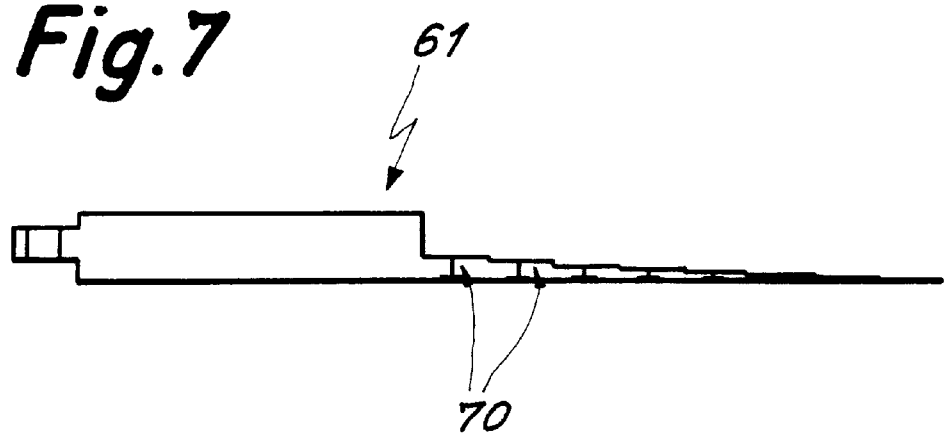
FIG. 7 is a side view of the leg of the tool shown in FIG. 6.

FIG. 7 shows the leg 61. Its thickness, similarly to the thickness of the not shown leg 62 is changed in a stepped manner over the leg length. The thickness of the individual stages corresponds to the desired shaft length of the auditory ossicles prosthesis. Depressions 70 are provided in the leg 61, and also in the not shown leg 62. The depressions preferably form semi-circular recesses. During cutting off of the prosthesis shaft, the shaft can be inserted in these semi-circular depressions, before the both legs are closed. The projecting region of the shaft is then cut off by a scalpel or a scissors.

Figure 8:
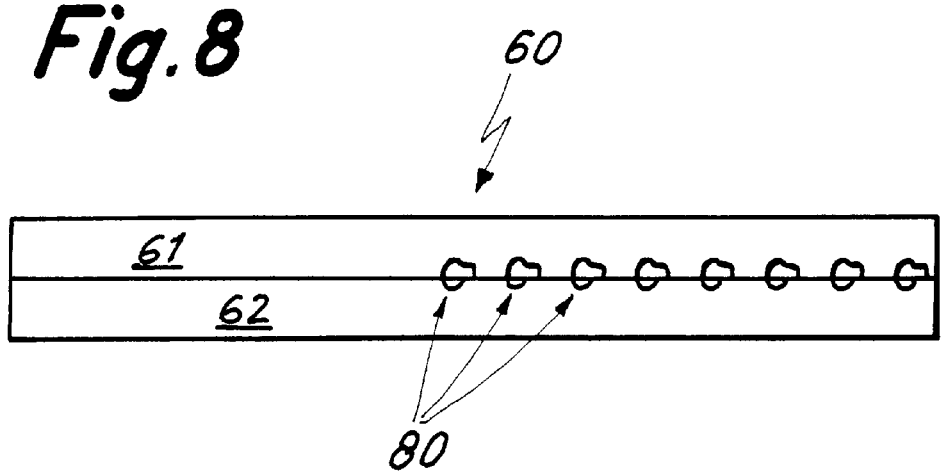
FIG. 8 is a view from below on the tool shown in FIG. 6.

FIG. 8 shows the tool 60 for adjustment of the shaft length from below. The both legs 61 and 62 are closed. The tool 60 has the depressions 80 for receiving the head plate. The head plate of the auditory ossicles prosthesis is clamped in the depressions 80, so that it can not fall out of the tool with the shaft mounted on it.

It will be understood that each of the elements described above, or two or more together, may also find a useful application in other types of constructions differing from the types described above.

While the invention has been illustrated and described as embodied in auditory ossicles prosthesis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention

What is claimed as new and desired to be protected by Letters Patent is set forth in the appended claims:

1. An auditory ossicles prosthesis, comprising a head plate for abutment against an eardrum; and a shaft arranged on said head plate for bridging a tympanic cavity from the eardrum up to a stirrup or a stirrup footplate, said shaft having an end spaced from said head plate and facing the stirrup and being provided at said end with a coupling member, said head plate having a throughgoing passage which extends radially inwardly of a periphery of said head plate and completely through a width of said head plate and is formed for receiving said shaft, so that said shaft can be received in said throughgoing passage and displaced in said throughgoing passage to extend outwardly beyond an outer side of said head plate and to be cut off to be adjusted, said passage being narrowable so that when said shaft is received in said passage and said passage is narrowed, said shaft is immovably fixed in said head plate, said passage having a periphery which is interrupted by a slot, said head plate having a deformable web located in a vicinity of said slot and said passage so that said slot and said passage can be narrowed by caulking of said web.

2. An auditory ossicle prosthesis as defined in claim 1, wherein said head plate is elliptic and has rounded edges.

3. An auditory ossicle prosthesis as defined in claim 1, wherein said shaft is provided with a scale.

4. An auditory ossicle prosthesis as defined in claim 1, wherein the prosthesis has a part with a side facing the eardrum or the stirrup, said side being roughened.

5. An auditory ossicle prosthesis as defined in claim 1, wherein said head plate, said shaft and said coupling member are laser-produced structural components.

6. An auditory ossicle prosthesis as defined in claim 1, wherein said head plate, said shaft and said coupling member are composed of a material selected from the group consisting of gold titanium.

7. An auditory ossicle prosthesis as defined in claim 1, wherein said coupling member is formed as a bell-shaped component.

8. An auditory ossicle prosthesis as defined in claim 7, wherein said head plate is elliptical, said bell-shaped component being provided with a slot, said slot extending parallel to a longitudinal semi-axis of said elliptical head plate.

9. An auditory ossicle prosthesis as defined in claim 8, wherein said slot in said bell-shaped component is 0.6 mm wide.

10. An auditory ossicle prosthesis as defined in claim 1, wherein said coupling member is formed as a plunger.

11. An auditory ossicle prosthesis as defined in claim 10, wherein said plunger has a diameter of 0.8 mm and is provided with a hollow space.

* * * * *